(12) United States Patent
Basque et al.

(10) Patent No.: US 7,344,671 B2
(45) Date of Patent: Mar. 18, 2008

(54) OPTICAL SEALING CLAMP AND A METHOD FOR SEALING AND CUTTING POLYMERIC SHEETS WITH A LASER

(75) Inventors: Roland Basque, Brossard (CA); Alain Cournoyer, Québec (CA); Marc Levesque, St-Augustin-de-Desmaures (CA)

(73) Assignee: Glopak Inc., St-Leonard (CA)

( * ) Notice: Subject to any disclaimer, the term of this patent is extended or adjusted under 35 U.S.C. 154(b) by 492 days.

(21) Appl. No.: 10/722,131

(22) Filed: Nov. 26, 2003

(65) Prior Publication Data

US 2005/0109452 A1    May 26, 2005

(51) Int. Cl.
B65B 51/10    (2006.01)

(52) U.S. Cl. ............ 264/400; 53/450; 53/451; 156/251

(58) Field of Classification Search .......... 264/400; 156/251
See application file for complete search history.

(56) References Cited

U.S. PATENT DOCUMENTS

| | | | |
|---|---|---|---|
| 3,989,778 A | 11/1976 | Osborne | |
| 4,069,080 A * | 1/1978 | Osborne | 456/272.8 |
| 4,532,753 A * | 8/1985 | Kovacs | 53/451 |
| 4,924,062 A | 5/1990 | Zurcher | |
| 4,945,203 A | 7/1990 | Soodak et al. | |
| 5,173,583 A | 12/1992 | de Contencin et al. | |
| 5,260,766 A * | 11/1993 | Armitage | 356/237.1 |
| 5,595,670 A | 1/1997 | Mombo-Caristan | |
| 5,630,308 A | 5/1997 | Guckenberger | |
| 5,659,479 A | 8/1997 | Duley et al. | |
| 5,701,725 A | 12/1997 | Neri et al. | |
| 5,911,665 A * | 6/1999 | Heydarpour et al. | 53/449 |
| 6,103,050 A | 8/2000 | Krueger | |
| 6,207,925 B1 * | 3/2001 | Kendall | 219/121.63 |
| 6,237,308 B1 | 5/2001 | Quintin et al. | |
| 6,387,209 B1 | 5/2002 | Nettesheim | |
| 6,670,574 B1 | 12/2003 | Bates et al. | |
| 6,818,857 B1 | 11/2004 | Cho et al. | |
| 2002/0008809 A1 | 1/2002 | Babuka et al. | |
| 2002/0144984 A1 | 10/2002 | Mori et al. | |

FOREIGN PATENT DOCUMENTS

| | | |
|---|---|---|
| EP | 0 472 850 A2 | 4/1992 |
| WO | WO 98/16430 | 4/1998 |

* cited by examiner

Primary Examiner—Mary Lynn Theisen
(74) Attorney, Agent, or Firm—Ogilvy Renault LLP (57) ABSTRACT

The invention is specially directed towards intermittent motion packaging machines where the packages are momentarily immobilized at a forming station for the time duration of the package sealing and cutting. The polymeric sheets or films are sealed and cut after being exposed to a laser beam in a controlled and optimized manner. The laser beam is shaped with appropriate optical elements to provide a desired intensity profile in the section of the films to be sealed or sealed and cut. With this method, a package can be sealed and cut simultaneously in one exposure step. An optical clamp holds the films together while they are being sealed by the laser. The optical clamp can reflect back to the films, partially or totally, the laser beam intensity that has not been previously absorbed. The optical clamp further allows to monitor the sealing and cutting process while the process is being performed.

64 Claims, 10 Drawing Sheets

OPTICAL SEALING CLAMP AND A METHOD FOR SEALING AND CUTTING POLYMERIC SHEETS WITH A LASER

CROSS-REFERENCE TO RELATED APPLICATIONS

The application is the first application for this invention.

FIELD OF THE INVENTION

The invention relates to a method and an apparatus to seal or cut polymeric sheets by laser radiation. More specifically, it relates to optically sealing and cutting with a laser polymeric sheets or films that are used in fast packaging machines such as high-speed forming, sealing and filling machines.

BACKGROUND OF THE INVENTION

In packaging industry, the welding and cutting of polymeric sheets is a very important issue. Polymeric materials are used to make all kinds of packages and in the case of food industry these packages can be for example pouches that contain liquid such as milk or sealed bags that contain solid food. For the food industry is it a requirement to have a packaging process that is reliable, of very high quality, and hygienic. Furthermore, the packaging process should be fast, efficient and easy to control.

In the industry of form/fill/seal packaging at high speed, conventional machines fall into two distinct categories, namely continuous and intermittent motion machines. In continuous motion machines, the packages are formed and sealed at a fixed speed and in intermittent motion machines, the package is momentarily immobilized at a cutting station for the time duration of the sealing process. Form/fill/seal packaging machines that are used to produce milk pouches are intermittent motion machines that can form/fill/seal milk pouches with typically a high rate of more than 1 liter per second. These machines use a heating system to seal and cut, in one operation step, the polymeric films therefore forming a bag or a pouch. Heating the polymeric films locally has the effect to weld the films together creating simultaneously two seals region separated by a region where the films are cut. The process must be well-controlled since too much heat can damage the integrity of the films whereas not enough heat will poorly weld the films.

In the industry of form/fill/seal packaging at high speed, the sealing systems that are generally in use utilize an electrical resistance wire that is heated by an electrical pulse. The heated wire is brought into contact with the films where the films are aimed to be sealed and cut, and the heat of the wire is transferred partially to the films therefore creating the seal. An example of this kind of machine can be found in U.S. Pat. No. 6,237,308 B1. Although this system allows for high speed packaging and is a well-mastered process, it has some drawbacks. The first drawback of this system is that the hot wire must be in contact (directly or indirectly via a disposable release sheet) with the films to transfer the heat to the films. This can lead to contamination problems and the hot wire and/or the release sheet must often be changed. The actual technique is also not a very efficient process since the film area that is heated via this process is much larger than what is really needed to make the seal. Finally, since the hot wire is located in a mechanical clamp that brings the films into contact, it is subject to mechanical vibrations that can affect the seal quality.

The use of lasers to seal and cut polymeric films in a continuous sealing apparatus is known from U.S. Pat. No. 6,207,925 B1. Three laser beams are controlled to perform the transverse seal-cut-seal action between two contiguous packages. Each laser is devoted to either seal or cut the films. Because of the continuous motion of the films, the time for the laser beams to perform the cut and seal is extended substantially to the whole package cycle. The teachings of U.S. Pat. No. 6,207,925 B1 cannot be readily adapted for use with intermittent motion form/fill/seal machines and the spot beam precision control in the case of continuous motion machines remains costly.

Therefore there is a need for a method and an apparatus for improving the sealing and cutting process of a high speed packaging machine, in order to increase the efficiency of the process, to reduce the mechanical contact between the heating source and the films, and to increase the overall lifetime of the machine components.

SUMMARY OF THE INVENTION

Accordingly, the object of the present invention is to provide a method of sealing and cutting optically polymeric films for packaging machines based on an optimized optical system using a laser or several lasers and a special optical clamp. The present invention can be applied to any polymeric sheets or films that require welding or cutting. The method allows for a more efficient optical sealing and cutting process in comparison with previous methods found in the prior art.

One feature of the present invention is to provide a method of sealing and cutting optically polymeric sheets or films with at least one laser beam having a shaped intensity profile for the purpose of obtaining in one exposition step a seal/cut/seal operation. The method comprises:

shaping the at least one laser beam intensity profile by using an optical device to provide the desired intensity profile;

superposing and bringing into contact at least two of said films together; and exposing an area of the films, the area being a seal-cut-seal volume, to the said desired intensity profile for the purpose of obtaining in one exposition step two sealed regions where the films are sealed together separated by a cut region where the films have been cut.

It is another feature of this invention to further improve the efficiency of the sealing and cutting process by having more of the laser beam intensity absorbed by the films, the method comprising:

superposing and bringing into contact at least two polymeric films together;

exposing an area of the films, the area corresponding to a sealing volume, to at least one laser beam, providing an incident laser intensity, for the purpose of sealing or cutting the films;

increasing an intensity of the laser beam in the sealing volume by re-injecting partly or totally the laser beam intensity that has not been absorbed by the films back to the films by using at least one reflective device, therefore improving the efficiency of the sealing or cutting method by having more light intensity of said incident laser intensity absorbed by the films.

It is another feature of the present invention to provide an optical sealing clamp to optically seal or cut polymeric sheets or films with at least one laser beam, the clamp comprising:

two jaws wherein at least one of said jaws can be moved to allow a closing and an opening of the clamp;

one of said jaws, being a contact jaw, to bring the films into contact;

the other jaw, being an optical jaw, having an optical window to let laser beams pass through it and wherein said window is wide enough to allow to optically seal or cut the whole width of said films; and support means to interconnect said jaws and to allow a controlled opening and closing of the clamp.

It is a further aspect of the above-described clamp to provide for an increase of the laser beam intensity in the films by having said contact jaw surface reflecting partially or totally the laser beam intensity that has not been absorbed by the films back to the films, therefore increasing the sealing and cutting process efficiency.

It is a further aspect of the above-described clamp to provide for an additional increase of the laser beam intensity in the films by having said optical jaw surface reflecting partially or totally the laser beam intensity that has not been absorbed by the films back to the films, therefore increasing even more the sealing and cutting process efficiency.

It is a further aspect of the above-described clamp to provide for an additional increase of the laser beam intensity in the films by having the surface of the jaws that are exposed to the unabsorbed laser intensity by the films profiled to allow for three back and forth reflections from one jaw to the other, allowing therefore for four passes of laser beam into the films.

It is another feature of the present invention to provide a method of monitoring the sealing and cutting process by optically imaging the seal and cut quality through the window of the clamp while the optical sealing and cutting process is being performed.

According to a still further broad aspect of the present invention there is provided two packaging methods that offer an improved sealing and cutting efficiency and that overcome or reduce some drawbacks of the prior art due to the direct contact of the heating source with the films, such as packages contamination and the short life-time of the sealing elements. Both methods are using at least one optical clamp the characteristics of which have been described above.

The first packaging method is a method of forming, sealing and cutting optically, and filling a pouch with a liquid at high speed. The method comprises:

providing a vertical tube, made of polymeric film, that is partially or totally filled with a liquid, or that is being filled with a liquid;

flattening a filled section of said tube for a determined time interval using an optical sealing clamp for subsequent optical sealing and cutting of said section of said tube;

iii)exposing said section of said tube to at least one laser beam intensity, for a time exposure interval T, to heat in a controlled manner said section of said tube, said intensity being shaped to obtain a desired intensity profile and to provide a corresponding absorbed intensity profile in said section of said tube;

iv)providing a desired heat amount to said section of said tube by optimizing a combination of said absorbed intensity profile, said time exposure interval, and by heating if required said optical sealing clamp;

v)obtaining as a result two seals across said section of said tube and simultaneously severing said tube between the seals, to form a top seal for a filled pouch that is separated form said tube and a bottom seal for said vertical tube.

The second packaging method is a method of sealing or sealing-and-cutting packages made with polymeric sheets or films using at least one laser source and at least one optical sealing clamp, the method comprising the steps of:

providing a partially or completely formed package that is partially or completely filled with its content or being filled with its content;

superposing and bringing into contact an inner wall of a section of said package for subsequent sealing by means of an optical sealing clamp;

exposing said section of said package to at least one laser beam intensity, for a time exposure interval $\tau$, to heat in a controlled manner said section of said package, said intensity being shaped to obtain a desired intensity profile and to provide a corresponding absorbed intensity profile in said section of said package;

providing a desired heat amount to said section of said package in order to perform either a sealing operation or a sealing-and-cutting operation, by optimizing a combination of said absorbed intensity profile, said time exposure interval, and by heating if required said optical sealing clamp;

obtaining as a result in the case of the sealing operation, a seal across said section of said package, and in the case of the sealing-and-cutting operation, two seals across said section of said package and simultaneously a cut region between the two seals where the package is cut.

The packaging methods described above can further provide for a monitoring of the sealing or sealing-and-cutting operation by inspecting, using an optical detection assembly, the package being sealed through the optical window of the optical sealing clamp, while the sealing or sealing-and-cutting operation is being performed.

The packaging methods described above can further comprise the partial or total re-injection of the laser beam intensity that has not been absorbed in step iii) by means of the reflective property of the optical sealing clamp, in order to enhance in a controlled manner heat in the section of the films that are to be sealed and cut.

BRIEF DESCRIPTION OF THE DRAWINGS

The preferred embodiments of the present invention will now be described with reference to the accompanying drawings in which.

It will be noted that throughout the appended drawings, like features are identified by like reference numerals.

DETAILED DESCRIPTION OF THE PREFERRED EMBODIMENT

Figure 1:
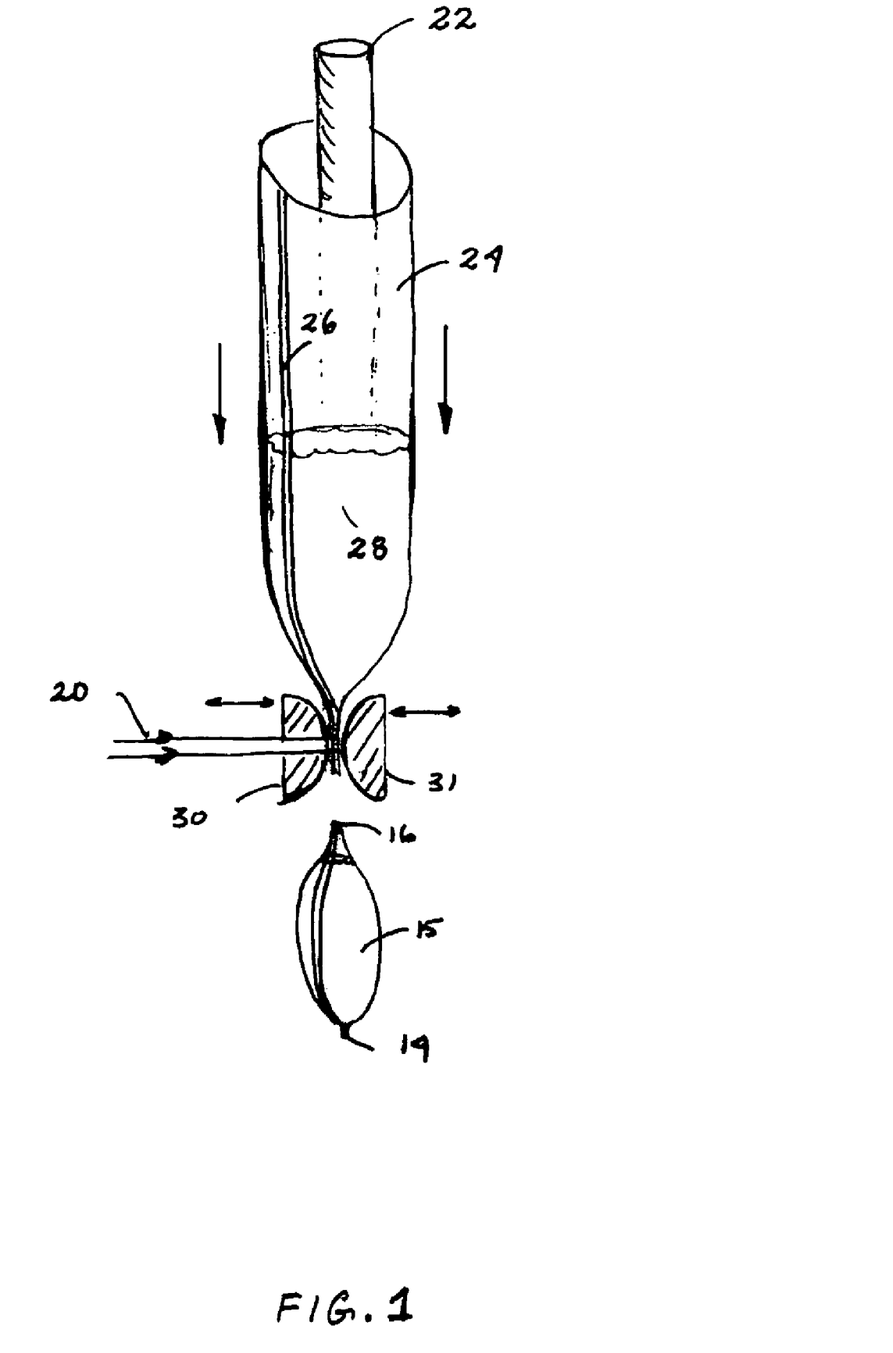
FIG. 1 is a drawing showing a vertical machine that is forming pouches, filling them with a liquid and sealing them.

In this detailed description of the preferred embodiment we will focus on food industry form/fill/seal intermittent machines (FFS) where the package is momentarily immobilized at a cutting station for the time duration of the sealing process. FIG. 1 is a schematic illustration of the preferred embodiment of this invention where a vertical form/fill/seal machine (VFFS) is shown. VFFS machines are commonly used to manufacture milk pouches. In this type of machine, a tube 24 made from a polymeric flexible film is continuously filled with a liquid 28 by a liquid delivering device 22. The tube 24 has been previously formed (not shown on this figure) from a roll of a polymeric flexible film that has been vertically sealed 26 using a vertical sealer clamp. A horizontal optical clamp having two jaws 30, 31 repeatedly opening and closing, allows for the production of filled pouches 15 at a rate of about 1 pouch per second. While being closed on the tube, the clamp momentarily immobilized it for the time duration of the sealing process, after which it reopened to leave passage to another length of tube.

The present invention proposes a method and a special optical clamp to improve the efficiency of the optical sealing and cutting process of flexible films in the context of high speed intermittent machines. It also presents a way to seal an cut flexible polymeric films with indirect contact between the heating system source and the films therefore reducing contamination problems. As shown in FIG. 1 a laser beam 20 passes through the first jaw 30, referred to as an optical jaw, and impinges on the two layers of the tube that have been previously brought into contact by closing the jaws 30, 31 of the clamp. The laser beam is absorbed by the films partially or totally in a volume referred to as the sealing volume and the absorbed energy heats the films causing the sealing process between the films. With enough absorbed energy in the sealing volume, the films will be cut. By controlling the amount of absorbed energy by the films it is possible in one operation to seal and cut the flexible films. It is a characteristic of the present invention, as it will be described later in this disclosure, to present a method to control and optimize the absorbed energy by the films.

Typically the films have a thickness less than 100 microns and they contain a large proportion of polyethylene. In the manufacturing of milk pouches, the transverse seals 14, 16 have a length of about 6 inches. The optical clamp therefore needs to have a length of at least 6 inches to seal a pouch.

Figure 2:
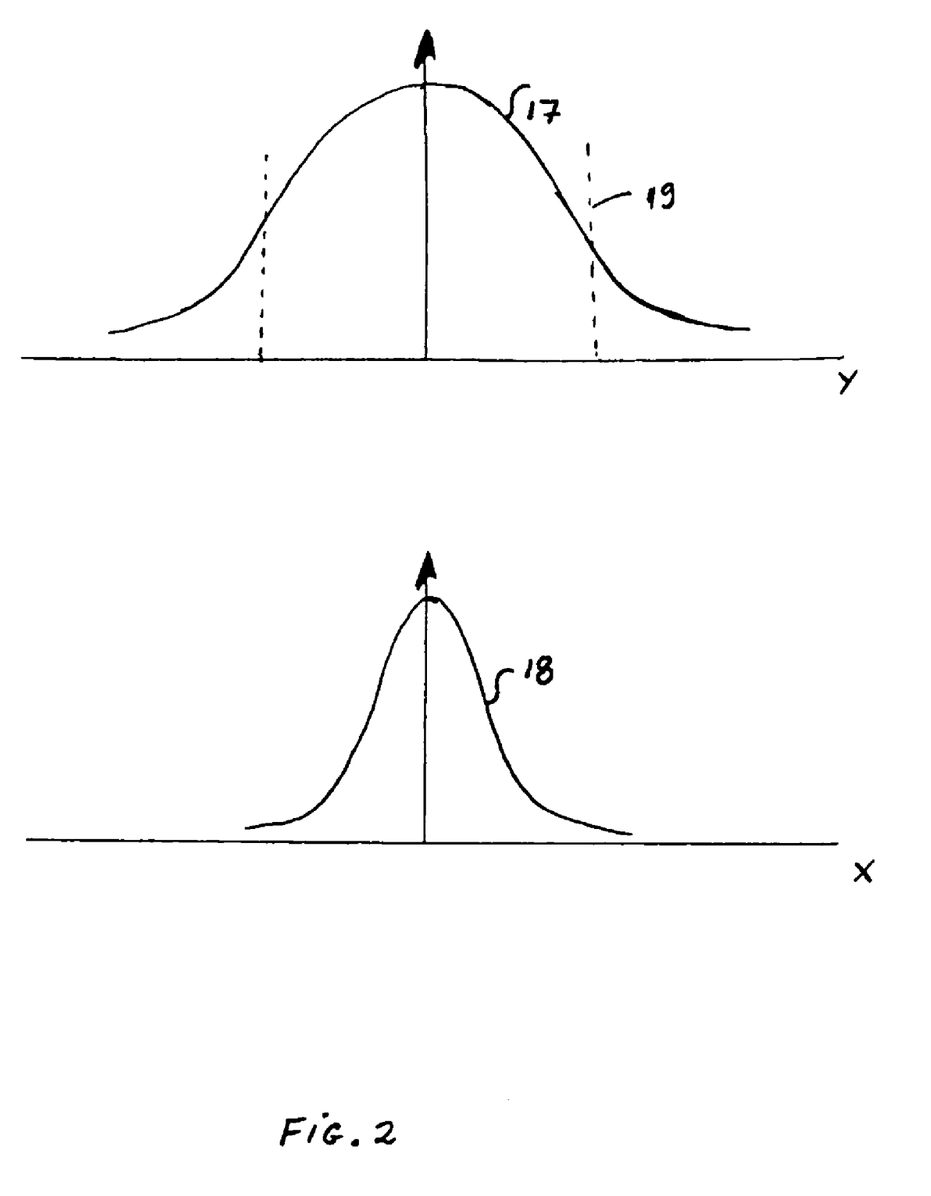
FIG. 2 is a graph showing the intensity distribution of the laser spot at the level of the films along the seal length (y axis) and in the perpendicular direction (x axis)

The laser used in this preferred embodiment is a $CO_2$ laser 50 emitting at a wavelength of 10.6 microns less than 100 watts of power. It will be understood by a person skilled in the art that another type of laser or a $CO_2$ laser emitting at another wavelength could as well be used. The $CO_2$ laser beam is shaped in order to get the desired intensity profile where the films have to be sealed or sealed and cut. The $CO_2$ laser beam 20 can by either focused to a spot of about 1 mm of diameter 53 at the level of the films or it can be shaped, using an appropriate optical device, in an elongated spot 58 that can cover the whole width (6 inches) of the films. In the first case, shown in FIG. 12, the laser beam is scanned over the films width sealing in about half a second the whole width of the films. In the second case, shown in FIG. 11, the laser beam shaped in a horizontally elongated spot impinges the films for about half a second. In both cases the time exposition of the films can be controlled by a switch 57 that can interrupt the laser beam. FIG. 2 illustrates the intensity profile of the laser spot on the surface of the films in the case of an elongated spot 58: along the seal length 17 and in the perpendicular direction 18. The hatched lines 19 on the graph are showing the films width extremities. The elongated beam is generally longer than the film width so that the incoming intensity is large enough to seal the films and to insure that the intensity along the sealing volume is not below an insufficient value. In the case where the laser spot is circular the distribution is the same in both axis and is similar to the distribution 18. By controlling the beam intensity profile by appropriate shaping of the beam, it is possible to control the absorbed energy distribution in the films. In particular an appropriate shaping on the laser beam will provide in one operation two seals regions separated by a region where the films are cut. This control of the absorbed energy distribution is a characteristic of the present invention.

The intensity absorbed by the films will depend on the impinging intensity and on the absorption capacity of the films. The type of films that are used to make milk pouches will typically absorb only about 10% of the laser intensity because of their thickness of only about 100 microns. Thicker films would of course absorb more and films having a special absorbing layer could also absorb a bigger portion of the impinging laser beam. However it is a feature of the present invention to provide a way to increase the absorbed light by the films by allowing for multi passes of the laser beam in the films as it will be discussed later in this disclosure.

The sealing and cutting process depends on many factors such as the amount of laser intensity that is absorbed, the distribution of the energy absorption within the films, the time exposition of the films, and on thermal characteristics of the films such as the thermal conductivity of the films. It was found in this preferred embodiment that high quality seals were obtained by exposing the films to a total energy of less than 100 Joules per $cm^2$. That corresponds in the case of a laser beam shaped into an elongated spot to an exposition time of less than a second to produce two high quality seals along the whole width of the films that are separated be a region where the films have been cut.

Figure 3A:
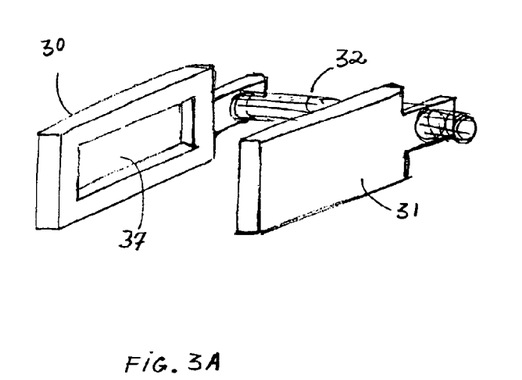
FIG. 3A and FIG. 3B are showing a clamp in opened position (3A) and in closed position (3B). One of the jaw has an aperture.
Figure 3B:
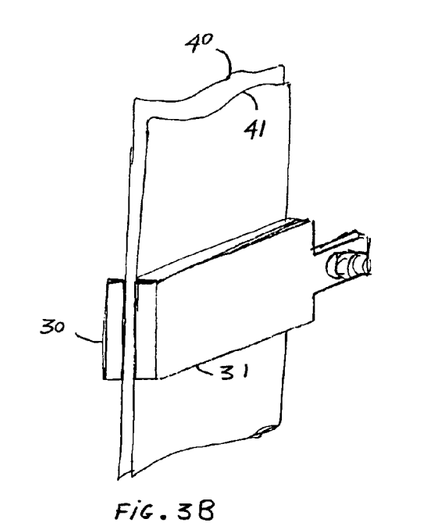
Figure 4:
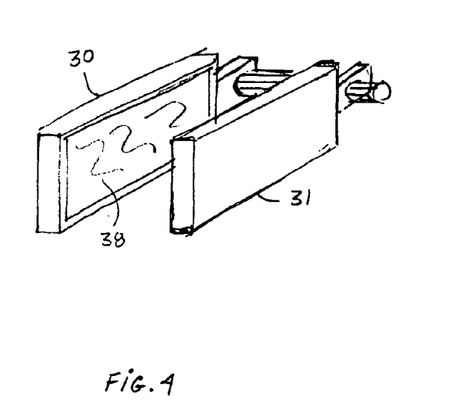
FIG. 4 is showing a clamp with a ZnSe window.
Figure 5:
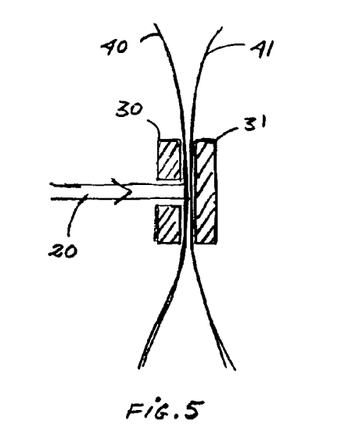
FIG. 5 is a side view of a clamp in a closed position. The clamp is bringing into contact two flexible polymeric films and an incoming laser beam is sealing and cutting the films.

We will now describe in more details several optical clamp designs that can be used in this invention to seal and cut the films. FIG. 3A illustrates the main parts of the clamp: the optical jaw 30 and the other jaw 31 can be moved via a mechanism 32 to a closed position as shown in FIG. 3B in order to bring in contact the two films 40 and 41 prior to the sealing process. The optical jaw is characterized by the fact that is has a window wide enough to allow sealing in a unique operation the whole width of the film. The laser beam 20 passes through that window to impinge on the films as shown in FIG. 5. The window can be an aperture 37 in a metallic structure has shown on FIG. 3A, it can also be an aperture covered by an optical material, it can be made completely of a transparent material 38, or it could be a mounting plate for a series of miniature lasers. The other jaw 31 can allow for reflecting back to the films the laser intensity that have not been absorbed in the first laser pass, increasing therefore the amount of laser light intensity available to the films.

Figure 6:
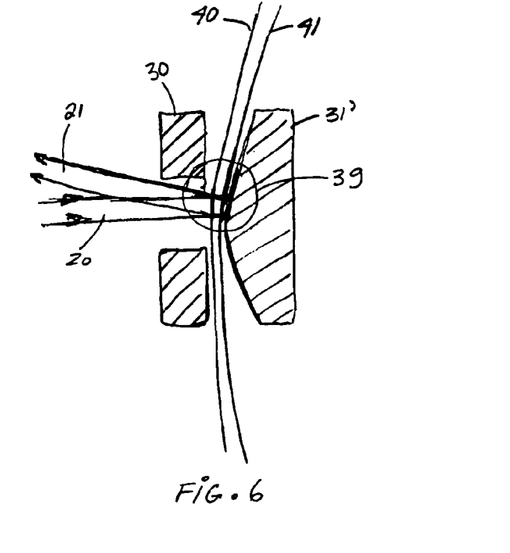
FIG. 6 is a side view of a clamp with one jaw profiled to apply a tension on the films and reflect partially or totally the light that was not absorbed by the films back to the films.

When the jaw 31 is meant to reflect partially or totally the incoming unabsorbed laser light, its surface can be a metallic polished. The jaw can also be profiled 31' as shown in FIG. 6 to apply a tension on the films while bringing them into contact. Tension needs to be controlled in the case of thin plastic films to avoid a stretching and thinning of the films before a seal or cut is effected.

Figure 7A:
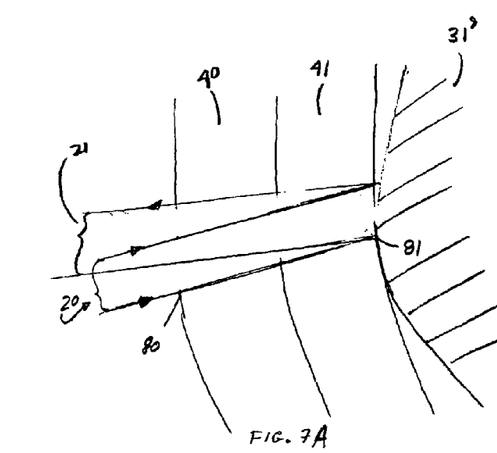
FIG. 7A is a close-up illustration of the sealing region where the incident laser beam is propagating across the two films and is reflected back by the jaw to the films. The evolution of the beam intensity along the sealing volume is shown below in the forward direction FIG. 7B and the backward direction (FIG. 7C).
Figure 7B:
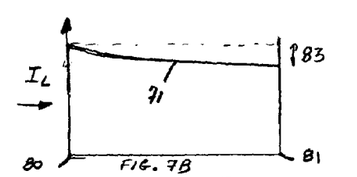
Figure 7C:
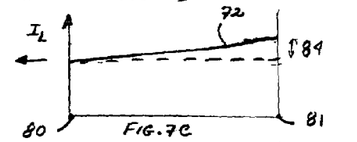
Figure 7D:
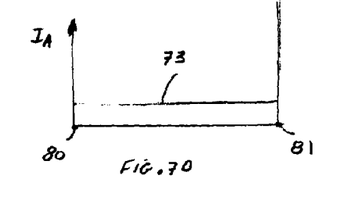
FIG. 7D shows the absorbed beam intensity.
Figures 7E, 7F:
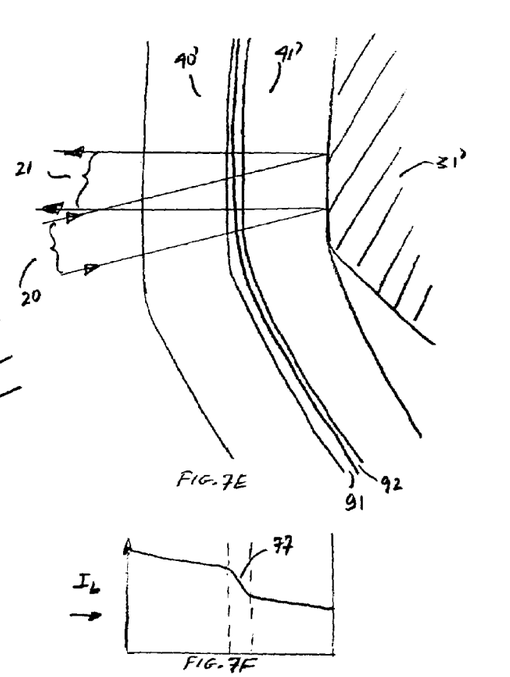
FIGS. 7E, 7F,7G, and 7H shows the same information in the case where the films are composed of one slightly absorbing layer and one strongly absorbing layer.
Figure 7G:
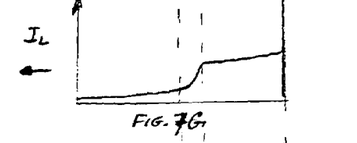
Figure 7H:
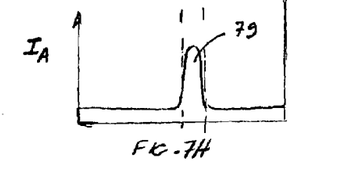

FIG. 7A is a close-up of the films sealing region 39 showing the incident laser beam 20 passing through the two films, the unabsorbed laser intensity is then hitting the contact jaw 31' that has been profiled to reflect it back 21 to the films. Since the films are absorbing a small portion of the laser intensity, this technique can allow ideally to roughly doubling the laser light in the sealing volume providing that the jaw 31' has a high reflectivity coefficient. The three following graphs show how the laser intensity changes along its propagation in the films due to its absorption by the films. FIG. 7B is showing how the laser intensity is reduced during its propagation through the films in the first pass 71 and FIG. 7C is showing how the laser intensity is reduced on its way back 72. After one pass, the laser intensity has been reduced by an amount 83 and in a second pass by an amount 84. That intensity has been absorbed 73 by the films as shown on FIG. 7D and is roughly twice the absorbed laser intensity of only one laser pass.

FIGS. 7E, 7F, 7G, and 7H show what happen when the films have a high absorption layer 91 or 92. Because of the layers high absorption capacity, the laser intensity is highly absorbed 79 at their level resulting in a non-uniform absorption and therefore to a non-uniform and localized heating of the films. In some cases a localized heating of the films may be a better approach than a uniform heating of the films.

Figure 8A:
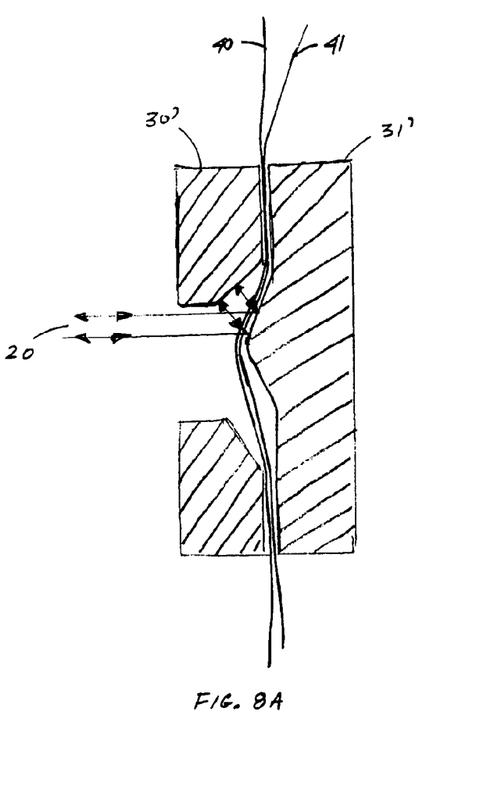
FIG. 8A is a side view illustration of a clamp with both jaws profiles to allow for 4 passes of the laser light in the films.
Figure 8B:
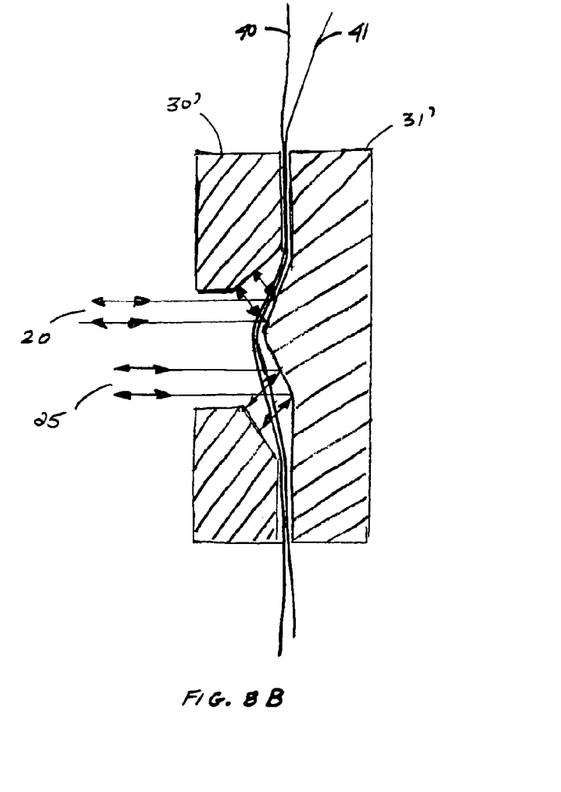
FIG. 8B shows the same clamp being used with two laser beams.
Figure 10:
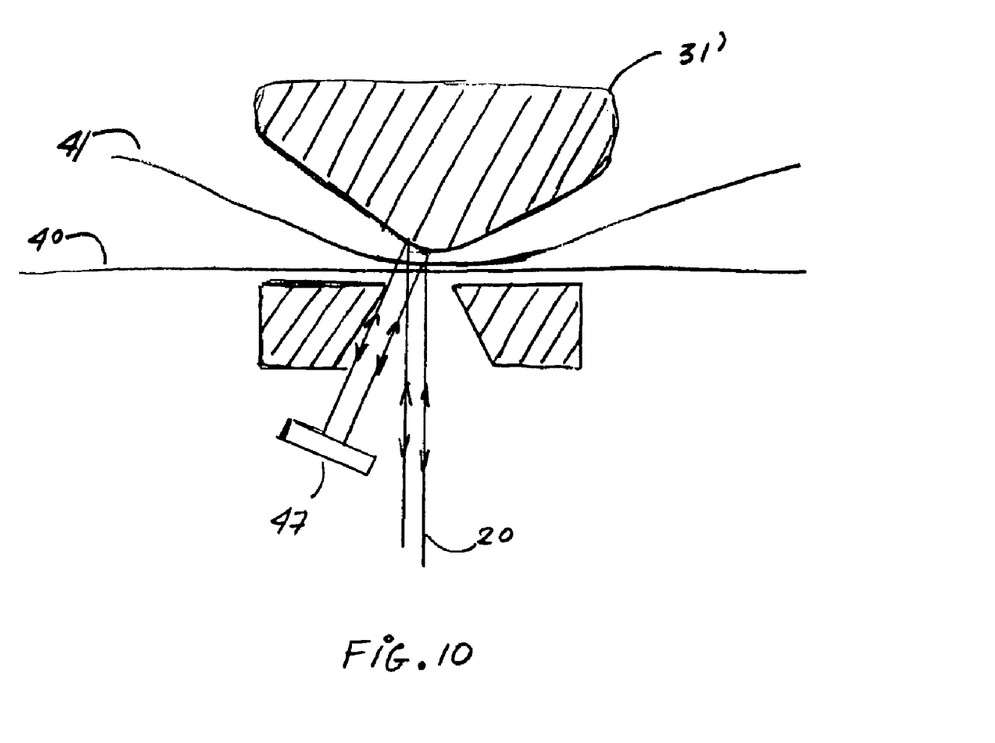
FIG. 10 is a side view of a clamp where a mirror attached to it reflects back to the film the unabsorbed light.

The optical clamp can also provide four passes of the laser beam 20 in the films. FIGS. 8A and 8B illustrate such a clamp. The optical jaw has a window that is profiled in order to reflect back to the films the unabsorbed laser light after the second laser pass. This embodiment provides an even higher efficiency of laser sealing and cutting of flexible polymeric films. Other profiles of the clamp's jaws can allow for multi-pass of the laser light through the films as it will be apparent to those skilled in the art. It will also be understood that the reflection process of the unabsorbed laser beam intensity can be provided by the use of reflection devices that are located externally of the window such as shown in FIG. 10 where a mirror 47 is used to reflect the unabsorbed light back to the films.

Figure 9:
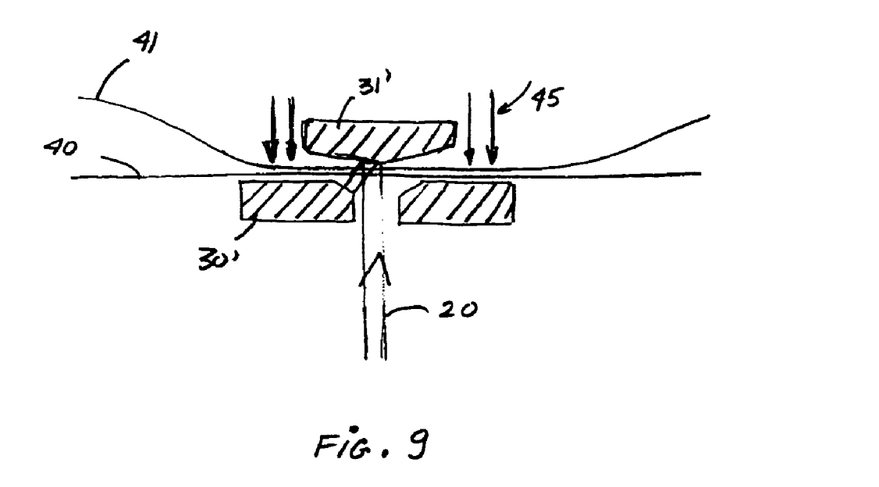
FIG. 9 shows a side view of a clamp using air streams to bring into contact the films.

The optical clamp can also be used in combination with an air system to bring into contact the films to be sealed. This is illustrated in FIG. 9 where pulsed air streams 45 are maintaining the films in contact while being sealed by the laser.

The optical clamp can naturally be used with more than one laser as illustrated in FIG. 8B where two beams, 20 and 25, are simultaneously sealing and cutting the films. This embodiment can add flexibility to the packaging system by enabling to control separately the sealing and the cutting process for example.

The clamp can furthermore be heated to help the sealing and cutting process by providing a pre-heating of the films.

All the above possible optical clamps designs provide a more efficient way to seal and cut flexible polymeric films or sheets as well as allowing for indirect contact between the heating system source (laser source) and the films therefore reducing contamination problems.

Figure 14:
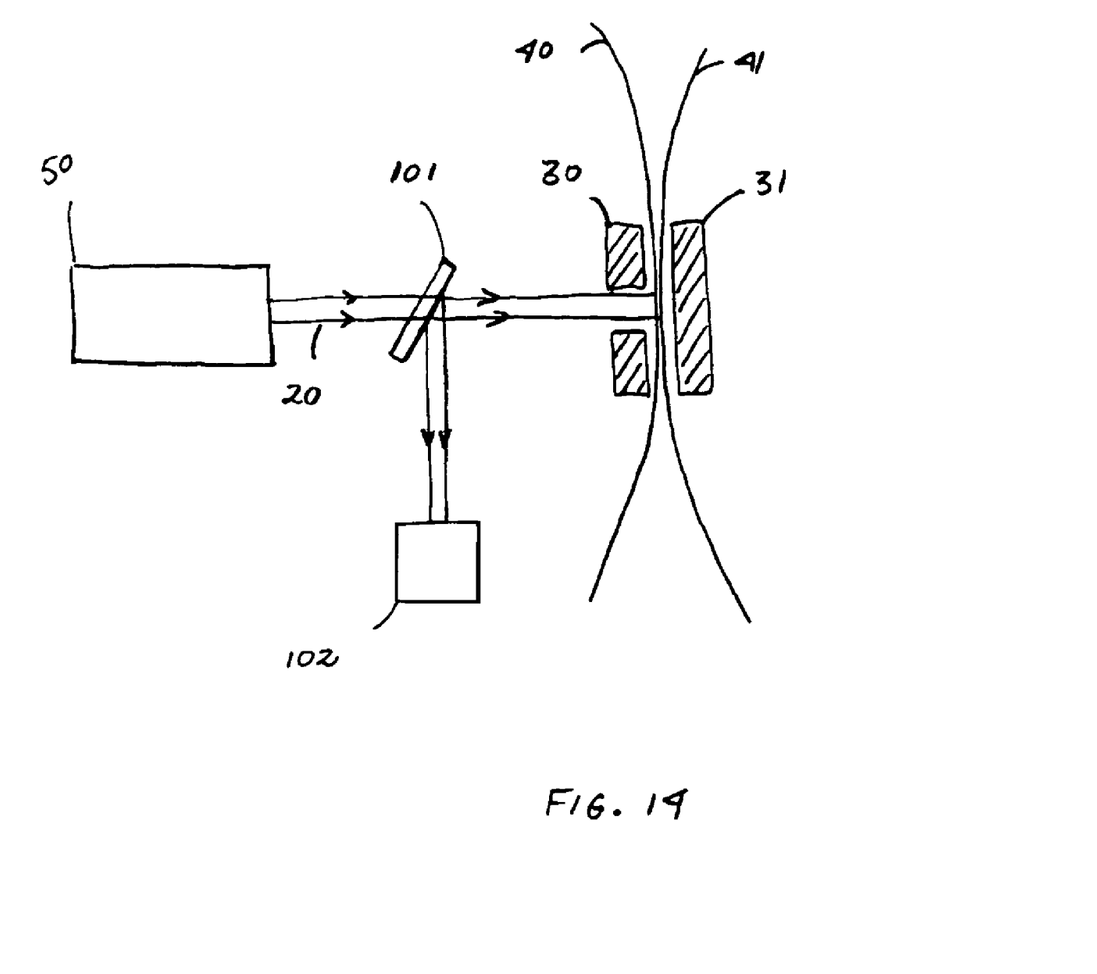
FIG. 14 is a schematic illustration of an optical set-up to monitor the sealing process of two films.

Furthermore all the above clamp designs allow inspecting the quality of the sealing or cutting operation of the films while these operations are being performed. An example of a possible way to realize this quality monitoring is shown in FIG. 14, where a beam splitter 101 has been inserted between the laser 50 and the optical jaw 30, enabling to optically inspect the seal quality as it is being performed. An optical assembly 102 comprising a detector and focusing optics is used to detect light intensity emitted by the films being sealed. Therefore some optical signature of the seal can be obtained and be used to control the sealing and cutting process.

Figure 11:
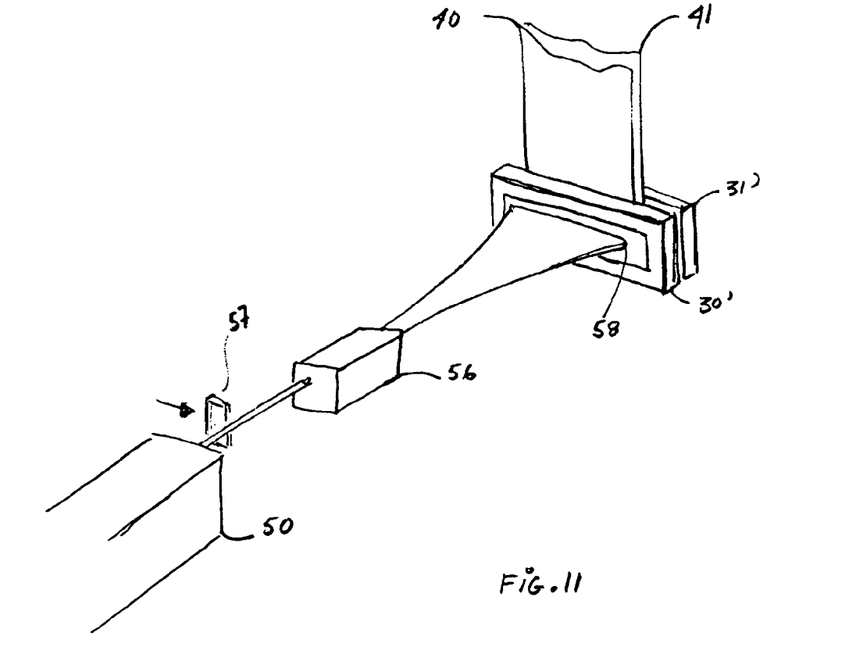
FIG. 11 is a schematic illustration of the optical system used to provide a laser elongated spot on the films to allow for the sealing and cutting of the whole films width.
Figure 12:
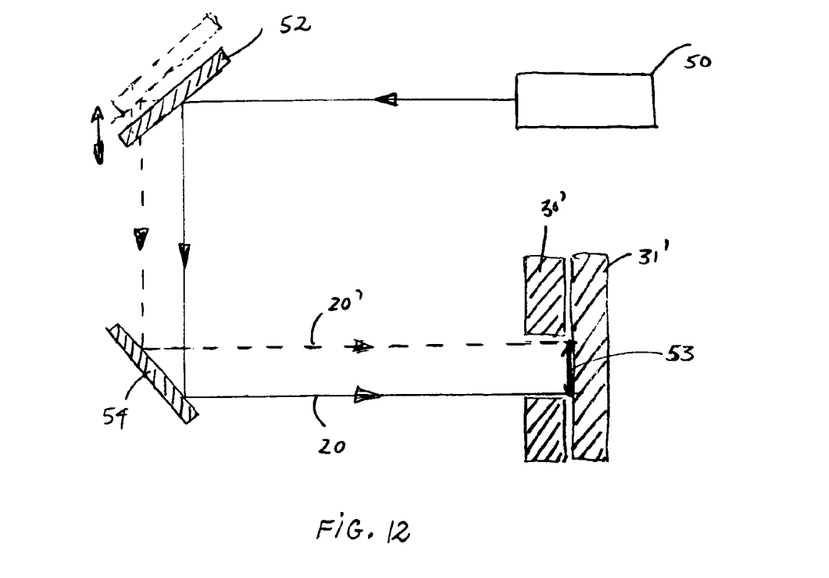
FIG. 12 is a schematic illustration (top view) of the laser beam scanning system that allows to seal and cut the whole width of the films. The clamp is shown from the top.

The clamps can allow for a scanning of a laser beam along the sealing volume or for an exposition of the films by an elongated laser beam. In both cases, the clamps allow sealing the whole film width via its window. FIG. 12 illustrates a possible scanning laser system where the laser beam 20 can be scanned along the sealing volume 53 by moving the mirror 52. FIG. 11 illustrates the case where the whole width of the film is exposed to an elongated laser spot 58. The laser beam intensity is shaped by an optical device 56 in this elongated spot. It will be appreciated by someone skilled in the art that other form of laser spots can as well be generated and used to seal and cut the films. Special laser beam shapes can be obtained with appropriate optical devices. The laser beam intensity profile is optimized via this shaping method to seal-cut-seal in one exposure step the films and therefore obtain two sealed regions where the films are sealed together separated by a cut region where the films have been cut.

Figure 13:
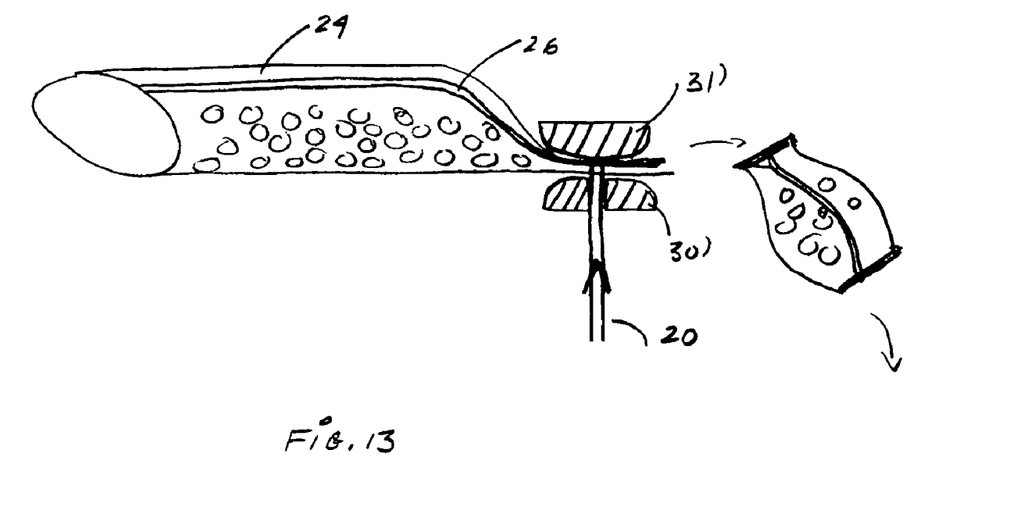
FIGS. 13, 13A, 13B, and 13C are schematic illustrations of other packaging systems.
Figure 13A:
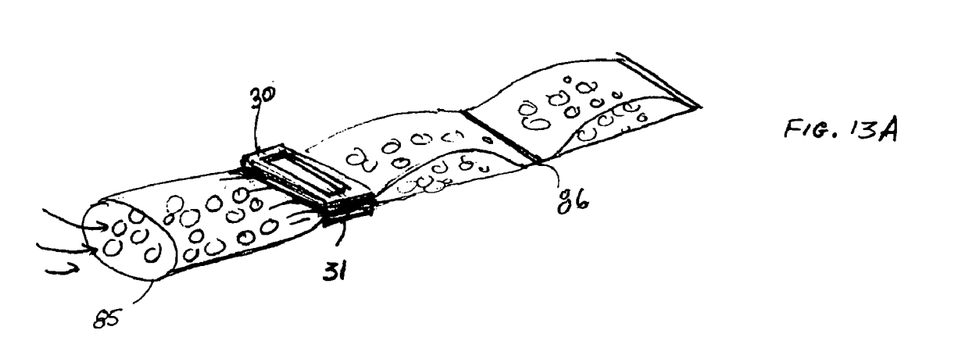
Figure 13B:
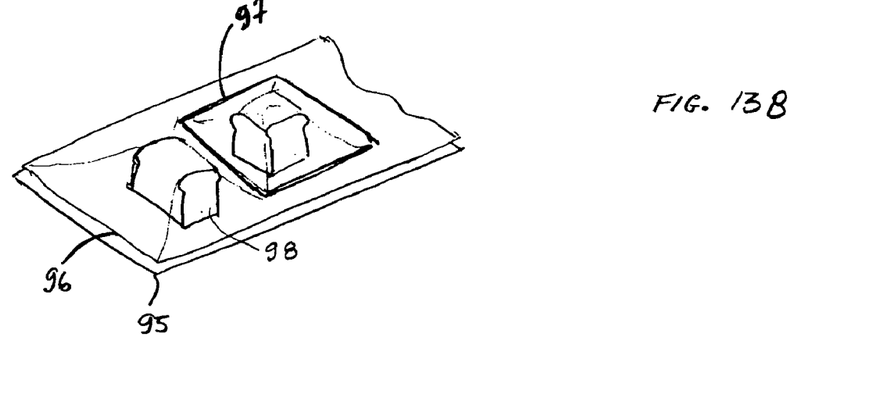
Figure 13C:
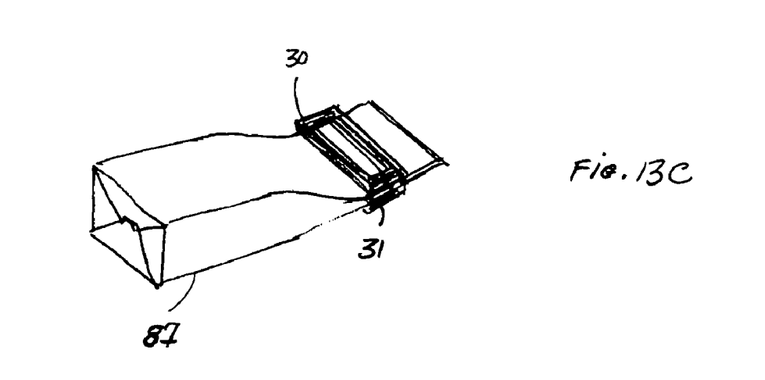

The present invention can as well be implemented for other packaging systems. FIGS. 13A, 13B, and 13C are examples of other embodiments of this invention where an optical clamp in combination with a laser is used to seal a package. FIG. 13A shows a tube filled 85 with solid food that has been sealed 86 by an optical clamp 30, 31. FIG. 13C is showing a bag being sealed by a laser using an optical clamp. FIG. 13B illustrates an aliment that has been in a first step placed on a polymeric sheet 95 and then covered by another polymeric sheet 96. The films 95, 96 are sealed and cut with a laser and using an optical clamp, a package is formed.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method of sealing or cutting optically with at least one laser beam flexible polymeric films, the method comprising:

superposing and bringing into contact at least two of said films together by actuating a support mechanism interconnecting two jaws of an optical clamp to allow a closing of the clamp whereupon said films are pressed between said jaws about an area to be sealed/cut with the area being free of contact with at least one of said jaws, exposing said area of the films to said at least one laser beam by directing the laser beam through an aperture of at least one of said jaws of said optical clamp, the area corresponding to a volume of said polymeric films to be sealed or cut, providing an incident laser beam intensity, for the purpose of one of sealing and cutting said films, increasing an intensity of the laser beam in the volume by re-injecting partly or totally an unabsorbed portion of the incident laser beam intensity that has not been absorbed by the films back to the films by using at least one reflective device, therefore improving the efficiency of the sealing or cutting method by having more light intensity of said incident laser intensity absorbed by the films.

2. The method as claimed in claim 1, wherein said unabsorbed laser intensity is at least 80% of said incident laser intensity.

3. The method as claimed in claim 1, wherein said unabsorbed laser intensity is at least 85% of said incident laser intensity.

4. The method as claimed in claim 1, wherein said unabsorbed laser intensity is at least 90% of said incident laser intensity.

5. The method as claimed in claim 1, wherein said exposing an area of the films comprises:

focusing on the films the laser beam into a small spot, scanning the small spot along the whole width of the films to obtain an elongated seal, and controlling the scanning to obtain a high quality seal.

6. The method as claimed in claim 5, wherein said scanning is continuous.

7. The method as claimed in claim 5, wherein said scanning is performed by using an optical set-up that comprises at least one mirror to scan the laser beam spot on the films.

8. The method as claimed in claim 1, wherein exposing of the films comprises shaping the laser beam into a line wherein said line is wide enough to cover the whole width of the films to be sealed.

9. The method as claimed in claim 1, wherein said re-injecting of unabsorbed laser intensity back to the films comprises reflecting said unabsorbed laser intensity off a reflective surface on one of said jaws.

10. The method as claimed in claim 9, wherein said reflective surface is profiled to reflect back toward the films the unabsorbed laser intensity in said volume with an intensity distribution essentially the same as the incident laser intensity.

11. The method as claimed in claim 10, wherein the surface of the jaws that are exposed to the unabsorbed laser intensity by the films are profiled to allow for a plurality of back and forth reflections from one jaw to the other, allowing therefore for a multi-pass of laser beam into the films.

12. The method as claimed in claim 10, wherein the surface of the jaws that are exposed to the unabsorbed laser intensity by the films are profiled to allow for three back and forth reflections from one jaw to the other, allowing therefore for four passes of laser beam into the films.

13. The method as claimed in claim 9 further comprising monitoring said one of sealing and cutting by inspecting, using an optical detection assembly, said area of the films through the aperture of the clamp, while the said one of sealing and cutting is being performed.

14. A method of optically sealing and cutting flexible polymeric films with a single laser beam having a shaped intensity profile, the method comprising:

shaping the intensity profile of the single laser beam with respect to a volume of the films to be exposed by using an optical device, the intensity profile of the single laser beam comprising a first intensity for a cut region in the volume, and a second intensity for each one of two sealed regions in the volume, superposing and bringing into contact at least two of said films together by actuating a support mechanism interconnecting two jaws of an optical clamp to allow a closing of the clamp whereupon said films are pressed between said jaws, and exposing an area of the films, the area being referred to as a seal-cut-seal volume, to said single laser beam, for the purpose of obtaining, in one exposure step, two sealed regions separated by a cut region as defined by the shaping of the intensity profile, the two sealed regions each defining a portion of the seal-cut-seal volume where the films are sealed together, and the cut region defining another portion of the seal-cut-seal volume where the films cut, and wherein by the time the cut region is performed, the sealed regions are sealed.

15. The method as claimed in claim 14, wherein the laser beam intensity profile is a Gaussian profile with a width.

16. The method as claimed in claim 14, wherein each of said sealed regions are being larger than said cut region.

17. The method as claimed in claim 14, wherein said beam shaping comprises the use of lenses.

18. The method as claimed in claim 14, wherein said laser beam intensity profile comprises an intensity profile having a dimension at least larger than a width of said films for the purpose of covering the whole width of the films to be sealed or cut.

19. The method as claimed in claim 14, wherein said shaping the laser beam intensity profile comprises focusing into a small spot the laser beam for the purpose of scanning said spot along the seal-cut-seal volume of the films.

20. The method as claimed in claim 14 further comprising monitoring said sealing and cutting by inspecting said sealed regions using an optical detection assembly.

21. The method as claimed in claim 20, wherein said optical detection assembly shares some of said optical elements.

22. A method of forming, sealing and cutting optically, and filling a pouch with a liquid at high speed, said method comprising the steps of:

i) providing a vertical tube, made of polymeric film, that is at least partially filled with a liquid;

ii) flattening a filled section of said tube by actuating a support mechanism interconnecting two jaws of an optical clamp to allow a closing of the clamp whereupon said films are pressed between said jaws about a section of the films to be sealed/cut, with the section being free of contact with at least one of said jaws, and for a determined time interval for subsequent optical sealing and cutting of said section of said tube;

iii) exposing said section of said tube to an intensity profile of at least one laser beam, for a time exposure interval τ, to heat in a controlled manner said section of said tube, said intensity profile being shaped to provide a corresponding absorbed intensity profile in said section of said tube;

iv) providing a desired beat amount to said section of said tube by optimizing a combination of said absorbed intensity profile, said time exposure interval τ, and by heating if required said optical sealing clamp;

v) obtaining as a result two seals across said section of said tube, and simultaneously severed region between the seals to form a top seal for a filled pouch that is separated from said tube and a bottom seal for said vertical tube.

23. The method as claimed in claim 22, wherein said providing a vertical tube comprises the steps of:

providing, in roll form, a polymeric film, drawing said film by drawings means, over a tube former to form said vertical tube having an overlapped vertical film edge, sealing said overlapped vertical edge with a vertical sealer to form a vertical seal, continuously feeding a liquid within said tube below said vertical sealer and above said optical sealing clamp.

24. The method as claimed in claim 22, wherein said optical sealing clamp comprises:

two jaws wherein at least one of said jaws can be moved to allow a closing and an opening of the clamp;

one of said jaws, being a contact jaw, to bring into contact a inner wall of said section of said tube;

the other jaw, being an optical jaw, having an optical window to let said at least one laser beam intensity pass through it, providing the exposing of the section of the to tube the laser beam, and wherein said window is wide enough to allow to optically seal or cut the whole width of said section of said tube; and support means to interconnect said jaws and to allow a controlled opening and closing of the clamp.

25. The method as claimed in claim 24, wherein said aperture comprises an optical window made of a material transparent to the laser beam.

26. The method as claimed in claim 24, wherein said contact jaw has a profile to compress said inner wall of said tube together either by applying pressure or tension on said tube at the point of sealing and cutting.

27. The method as claimed in claim 26, wherein said support means comprises an interconnection on at least one end of said jaws that leaves a free space between the jaws to let the tube pass through and wherein said support means provides for said opening to be large enough to allow for said filled pouch to pass through.

28. The method as claimed in claim 24, further comprising re-injecting, at least partially, said laser beam intensity that has not been absorbed in step iii) by means of a reflective property of said optical sealing clamp, to enhance in a controlled manner said desired heat in the said section of said tube.

29. The method as claimed in claim 28, wherein said contact jaw has a profiled surface that reflects partly or totally the laser beam intensity that has not been absorbed in step iii) back to the tube.

30. The method as claimed in claim 29, wherein said optical jaw has a profiled surface that reflects partly or totally the laser beam intensity that has not been absorbed by the tube back to the tube.

31. The method as claimed in claim 30, wherein the surface of the jaws are profiled to allow for a plurality of back and forth reflections from one jaw to the other, allowing therefore for a multi-pass of the laser beam intensity into the films.

32. The method as claimed in claim 30, wherein the surface of the jaws are profiled to allow for three back and forth reflections from one jaw to the other, allowing therefore for four passes of the laser beam intensity into the films.

33. The method as claimed in claim 22, wherein said exposing comprises:

focusing on said section of said tube the laser beam intensity into a small spot;

scanning the small spot along the whole width of said section of said tube to obtain an elongated seal; and controlling the scanning to obtain a high quality seal.

34. The method as claimed in claim 33, wherein said scanning is continuous in time.

35. The method as claimed in claim 33, wherein said scanning is performed by using an optical set-up that comprises at least one mirror to scan the laser beam spot on the films.

36. The method as claimed in claim 22, wherein said exposing said section of said tube comprises shaping the laser beam into a line wherein said line is wide enough to cover the whole width of the section of the tube to be sealed.

37. The method as claimed in claim 22, wherein the desired intensity profile is a Gaussian profile with a width.

38. The method as claimed in claim 22, wherein said beam intensity being shaped is performed by using a lenses and optical filters assembly.

39. The method as claimed in claim 22, wherein said desired intensity profile comprises an intensity profile having a dimension at least larger than the width of said tube for the purpose of covering the whole width of the tube to be sealed and cut.

40. The method as claimed in claim 24 further comprising monitoring said sealing and cutting while said seals are being performed by inspecting, using an optical detection assembly, said section of said tube through the optical window of the optical sealing clamp.

41. A method of sealing or sealing-and-cutting packages made with polymeric films using at least one laser source and at least one optical sealing clamp, the method comprising the steps of:

i) providing a partially or completely formed package that is partially or completely filled with its content or being filled with its content;

ii) superposing and bringing into contact an inner wall of a section of said package for subsequent sealing by actuating two jaws of an optical sealing clamp to allow a closing of the clamp whereupon said films are pressed said jaws about said section of said films to be sealed/cut, the section being free of contact with at least one of said jaws;

iii) exposing for a time exposure interval τ, said section of said package to an intensity profile of at least one laser beam by directing the laser beam through an aperture of at least one of said jaws of the clamp to heat in a controlled manner said section of said package, said intensity profile being shaped to provide a corresponding absorbed intensity profile is said section of said package;

iv) providing a desired heat amount to said section of said package in order to perform one of a sealing operation and a sealing-and-cutting operation, by optimizing a combination of said absorbed intensity profile, said time exposure interval, and by heating said optical sealing clamp upon demand;

v) obtaining as a result in the case of the sealing operation, a seal across said section of said package, and in the case of the sealing-and-cutting operation, two sealed region across said section of said package and simultaneously a cut region between the two sealed regions where the package is cut.

42. The method as claimed in claim 41, wherein step i) comprises:
providing, in roll form, two polymeric film sheets,
drawing one of said film sheets over a packaging station where the content of the package is deposited on the film,
drawing the second film sheet over said content to form said partially formed package.

43. The method as claimed in claim 41, wherein step i) comprises providing a tube made of polymeric film.

44. The method as claimed in claim 41, wherein step i) comprises providing a bag made of a polymeric film.

45. The method as claimed in claim 41, wherein one of said two jaws is a movable jaw to allow a closing and an opening of the clamp;
one of said jaws, being a contact jaw, to bring into contact said inner wall of said section of said package;
the other jaw, being an optical jaw, having an aperture to let said at least one laser beam intensity pass through it, providing the exposing of the section of the package to the laser beam, and wherein said aperture is wide enough to allow said one of an optically sealing and optically cutting of the whole width of said section of said package; and
support means to interconnect said jaws and to allow a controlled opening and closing of the clamp.

46. The method as claimed in claim 45, wherein said aperture comprises an optical window made of a material transparent to the laser beam.

47. The method as claimed in claim 45, wherein said contact jaw has a profile to compress said inner wall of said package together either by applying pressure or tension on said package at the point of sealing and cutting.

48. The method as claimed in claim 47, wherein said support means comprises an interconnection on at least one end of said jaws that leaves a free space between the jaws to let the package pass through and wherein said support means provides for said opening to be large enough to allow for said filled package to pass through.

49. The method as claimed in claim 45, further comprising re-injecting, partially or totally, said laser beam intensity that has not been absorbed in step iii) by means of a reflective property of said optical sealing clamp, to enhance in a controlled manner heat in the said section of said package.

50. The method as claimed in claim 49, wherein said contact jaw has a profiled surface that reflects at least the laser beam intensity that has not been absorbed in step iii) back to the package.

51. The method as claimed in claim 50, wherein said optical jaw has a profiled surface that reflects at least partially the laser beam intensity that has not been absorbed by the package back to the package.

52. The method as claimed in claim 51, wherein the surface of the jaws are profiled to allow for a plurality of back an forth reflections from one jaw to the other, allowing therefore for a multi-pass of the laser beam intensity into the films.

53. The method as claimed in claim 51, wherein the surface of the jaws are profiled to allow for three back and forth reflections from one jaw to the other, allowing therefore for four passes of the laser beam intensity into the films.

54. The method as claimed in claim 41, wherein said exposing comprises:
focusing on said section of said section of said package the laser beam intensity into a small spot;
scanning the small spot along the whole width of said section of said package to obtain an elongated seal; and
controlling the scanning speed to obtain a high quality seal.

55. The method as claimed in claim 54, wherein said scanning is continuous time.

56. The method as claimed in claim 54, wherein said scanning is performed by using an optical set-up that comprises at least one mirror to scan the laser beam spot on the films.

57. The method as claimed in claim 41, wherein said exposing said section of said package comprises shaping the laser beam into a line wherein said line is wide enough to cover the whole width of the section of the package to be sealed.

58. The method as claimed in claim 41, wherein the desired intensity profile is a Gaussian profile with a width.

59. The method as claimed in claim 41, wherein said beam intensity being shaped is performed by using a lenses and optical filters assembly.

60. The method as claimed in claim 41, wherein said desired intensity profile comprises an intensity profile having a dimension at least larger than the width of said package for the purpose of covering the whole width of the package to be sealed and cut.

61. The method as claimed in claim 45 further comprising monitoring said one of a sealing and a sealing-and-cutting operation by inspecting, using an optical detection assembly, said section of said package through the aperture of the optical sealing clamp, while said one of a sealing and a sealing-and-cutting operation is being performed.

62. A method of sealing or cutting optically with at least one laser beam polymeric sheets, the method comprising:
superposing and bringing into contact at least two of said sheets together by actuating a support mechanism interconnecting two jaws of an optical clamp to allow a closing of the clamp whereupon said films are pressed between said jaws about an area of said sheets,
exposing the area of the sheets, to the at least one laser beam by directing the laser beam on the area, through an aperture of at least one of said jaws of the clamp, the area corresponding to at least a portion of a volume of said sheets to be sealed or cut
providing an incident laser beam intensity, for the purpose of one of sealing and cutting said sheets,
increasing an intensity of the laser beam in the volume by re-injecting partly or totally an unabsorbed portion of the incident laser beam intensity that has not been absorbed by the sheets back to the sheets by using at least one reflective device, the at least one reflective device dividing the unabsorbed portion of the incident laser beam intensity in at least two reflected laser beams each for increasing the intensity in a different portion of the volume, thereby improving the efficiency of the sealing or cutting method by having more light intensity of said incident laser intensity absorbed by the sheets.

63. A method of optically sealing and cutting polymeric sheets with a single laser beam having a shaped intensity profile, the method comprising:

shaping the intensity profile of the single laser beam with respect to a volume of the films to be exposed by using an optical device, the intensity profile of the single laser beam comprising a first intensity for a cut region in the volume, and a second intensity for each one of two sealed regions in the volume, superposing and bringing into contact at least two of said sheets together by actuating a support mechanism interconnecting two jaws of an optical clamp to allow a closing of the clamp whereupon said films are pressed between said jaws, and exposing an area of the sheets to said single laser beam, the area being referred to as a seal-cut-seal volume, to said single laser beam by directing said desired intensity through an aperture of the clamp for the purpose of obtaining, in one exposure step, two sealed regions separated by a cut region as defined by the shaping of the intensity profile, the two sealed regions each defining a portion of the seal-cut-seal volume where the sheets are sealed together and the cut region defining another portion of the seal-cut-seal volume where the sheets are cut, and wherein by the time the cut region is performed, the sealed regions are sealed.

64. A method of sealing or sealing-and-cutting packages made with polymeric sheets using at least one laser source and at least one optical sealing clamp, the method comprising the steps of:

i) providing a partially or completely formed package that is partially or completely filled with its content or being filled with its content, ii) superposing and bringing into contact an inner wall of a section of said package for subsequent sealing by actuating two jaws of an optical sealing clamp to allow a closing of the clamp whereupon said films are pressed between said jaws about the section to be sealed/cut, the section being free of contact with at least one of said jaws, iii) exposing for a time exposure interval $\tau$, said section of said package to an intensity profile of at least one laser beam by directing the laser beam through an aperture of at least one of said jaws of the clamp, to heat in a controlled manner said section of said package, said intensity profile being shaped to provide a corresponding absorbed intensity profile in said section of said package, iv) providing a desired heat amount to said section of said package in order to perform one of a sealing operation and a sealing-and-cutting operation, by optimizing a combination of said absorbed intensity profile, said time exposure interval, and by heating if required said optical sealing clamp, v) obtaining as a result in the case of the sealing operation, a seal across said section of said package, and in the case of the sealing-and-cutting operation, two sealed regions across said section of said package and simultaneously a cut region between the two sealed regions where the package is cut.

\* \* \* \* \*